United States Patent [19]

Baraona

[11] Patent Number: 4,543,528
[45] Date of Patent: Sep. 24, 1985

[54] FLEXIBLE PROBE ASSEMBLY FOR USE IN NONDESTRUCTIVE TESTING OF A CONVEX WORKPIECE SURFACE

[75] Inventor: John P. Baraona, Parma, Ohio

[73] Assignee: Republic Steel Corporation, Cleveland, Ohio

[21] Appl. No.: 476,772

[22] Filed: Mar. 18, 1983

Related U.S. Application Data

[63] Continuation-in-part of Ser. No. 431,213, Sep. 30, 1982, abandoned.

[51] Int. Cl.$^4$ .............. G01N 27/72; G01R 33/12
[52] U.S. Cl. ........................... 324/262; 324/243
[58] Field of Search .................... 324/219–221, 324/242, 243, 262, 261, 237, 238

[56] References Cited

U.S. PATENT DOCUMENTS

| | | | |
|---|---|---|---|
| 1,893,074 | 1/1933 | Drake | 324/242 |
| 2,250,458 | 7/1941 | Barnes | 324/226 |
| 2,526,977 | 10/1950 | Smith | 324/241 |
| 2,622,126 | 12/1952 | Bender et al. | 324/220 |
| 2,980,850 | 4/1961 | Cochran | 324/242 |
| 3,244,972 | 4/1966 | Fisher | 324/226 |
| 3,299,349 | 1/1967 | Tompkins et al. | 324/262 |
| 3,327,206 | 6/1967 | Wood et al. | 324/261 |
| 3,523,241 | 8/1970 | Barton | 324/260 |
| 3,568,049 | 3/1971 | Barton | 324/262 |
| 3,593,120 | 7/1971 | Mandula, Jr. et al. | 324/261 |
| 3,746,972 | 7/1973 | Mandula, Jr. et al. | 324/226 |
| 4,101,832 | 7/1978 | Baker et al. | 324/227 |
| 4,247,819 | 1/1981 | Shimada et al. | 324/233 |
| 4,303,884 | 12/1981 | Malick | 324/220 |

Primary Examiner—Gerard R. Strecker
Assistant Examiner—Walter E. Snow
Attorney, Agent, or Firm—Watts, Hoffman, Fisher & Heinke Co.

[57] ABSTRACT

A flexible test assembly is disclosed for use in nondestructive testing of ferrous objects of a variety of cross-sections. Spaced test heads are fixed to a non-magnetic, flexible band member. Each test head includes a body which houses a test probe. The flexible band member is connected to a clevis assembly through a spring biased double hinged connecting assembly. An urging means urges the clevis toward a workpiece surface to bring wear shoes of the test heads into engagement and tension the flexible test assembly into conformity with the surface of the workpiece.

18 Claims, 5 Drawing Figures

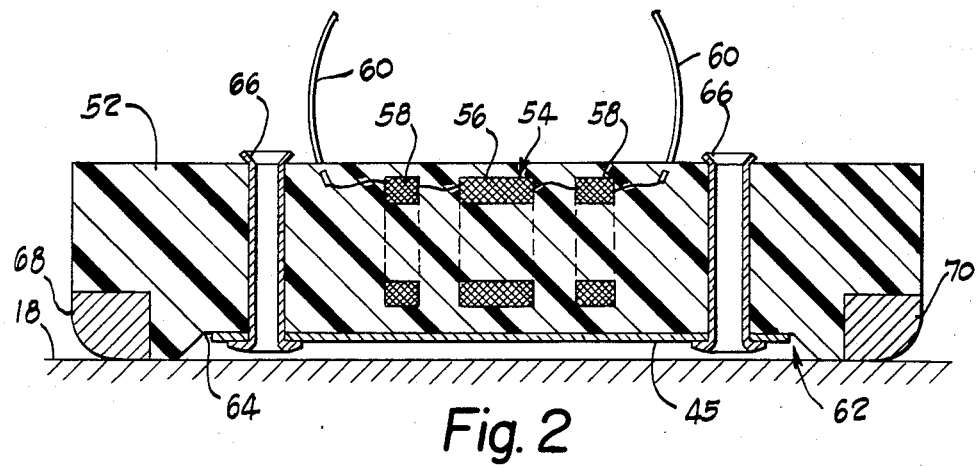
Fig. 2
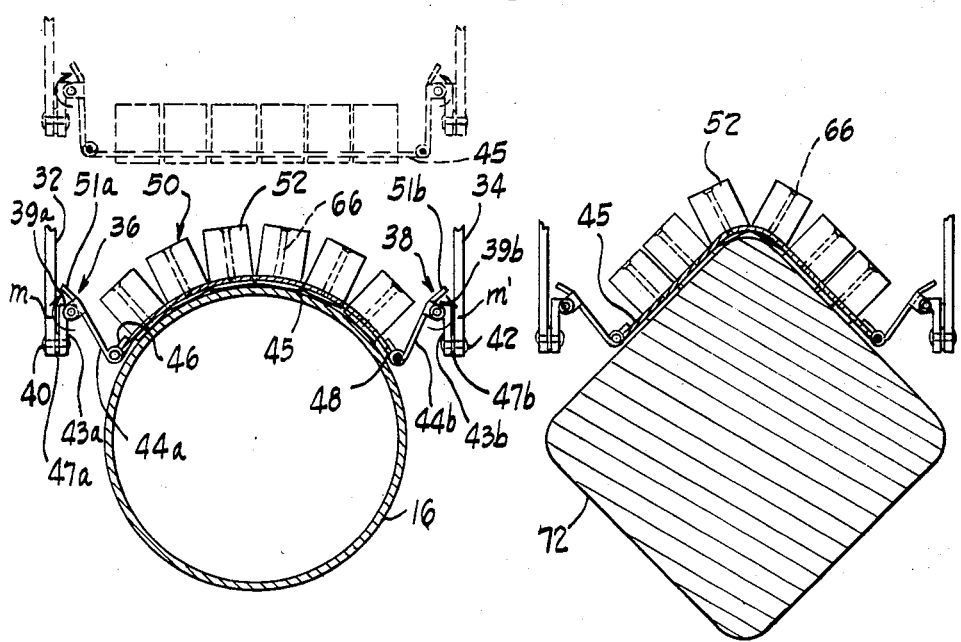
Fig. 3
Fig. 4

4,543,528

FLEXIBLE PROBE ASSEMBLY FOR USE IN NONDESTRUCTIVE TESTING OF A CONVEX WORKPIECE SURFACE

This is a continuation-in-part of the patent application Ser. No. 431,213 filed Sept. 30, 1982, now abandoned.

TECHNICAL FIELD

The present invention relates to an apparatus for use in nondestructive testing and more particularly to a flexible probe assembly for eddy current testing. The assembly conforms to a surface of a ferrous workpiece as the workpiece is tested.

BACKGROUND ART

Nondestructive testing of ferromagnetic objects by use of eddy currents is well known. This type of testing establishes eddy currents in a workpiece being tested which in turn establishes flux fields. A flaw or defect in the workpiece causes discontinuities in eddy current flow and result in corresponding discontinuities in the flux field. When a detection coil is moved along the workpiece, flux field variations are sensed as it passes over a flaw.

Multiple probe eddy current flaw detection devices are known for inspecting the entire circumference of an object, such as a tube or pipe, for the presence of defects. One such detection device includes a plurality of pickup arms mounted in spaced relationship around a workpiece travel path. Each of the pickup arms carries a set of sensing coils. Each pickup arm is mounted to pivot on an axis transverse to the direction of the travel path so that the sensing coil sets may be moved to closely surround a workpiece as it travels along the path.

Such a device is disclosed in U.S. Pat. No. 4,101,832 to Baker et al which has been useful to detect the presence of defects in an entire surface of a workpiece such as a pipe. In the Baker patent, each coil set is pre-formed for the inspection of workpieces, all of which have essentially the same uniform cross-sectional configuration from end to end. When utilizing the Baker et al device to inspect pipe, the detector sets are configured for the inspection of pipe of a given predetermined diameter. To change, for example, from inspection of six inch pipe to ten inch diameter pipe using the Baker et al device, it is necessary to install new detector sets configured to a larger diameter.

Another defect detecting apparatus is disclosed in U.S. Pat. No. 3,593,120 to Mandula, Jr. This apparatus includes a test probe that moves rotationally about the object being tested. The apparatus comprises a yoke having a pair of arms flexibly connected to and spanned by a chain of rolling members supporting a test probe. The rolling chain travels on the surface of the article so that the single probe is spring biased into testing contiguity not only with flat surfaces but also with rounded corners and curved surfaces of an article being tested such as a billet. The probe and the article being tested move in relative rotational and linear motion so that the probe spirally scans the inspected surface.

The Mandula device, does not provide the capability of multiprobe testing of the type that circumferentially surrounds a workpiece. Moreover, the rotational and linear relative motion is obviously more difficult to achieve than in simple linear motion as used by Baker et al.

DISCLOSURE OF THE INVENTION

The apparatus of this invention provides a new and improved multiple probe eddy current flaw detecting device that is particularly adapted for nondestructive testing of ferrous objects of any of a variety of cross-sections. The apparatus includes a test probe assembly which enables the testing of objects of a variety of shapes by tensioning a flexible test probe subassembly into conformity with a surface of an object under test.

In the disclosed and preferred embodiment, the test probe assembly includes a non-magnetic, flexible band which, when in use, is oriented transversely with respect to a workpiece path of travel. A plurality of closely spaced test probe heads are connected to the band. An urging mechanism is operatively connected to the flexible band near its ends to urge the probe heads it carries against a surface of a workpiece. The coaction of the urging mechanism and the flexible band maintains the heads in juxtaposition with a test object and thus in testing contiguity with it.

The preferred urging mechanism includes a clevis which is pivotally connected to the flexible band by two spaced connecting members. The connecting members are pivotally connected to the opposed ends of the flexible band member and each is pivotally connected to arms of the clevis. The connecting members are spring biased to tension the flexible member between the clevis arms.

Each test head is fixed to the flexible band member essentially only in a single plane which, when the apparatus is in use, allows each test head to "rock" transversely of the path of travel. This rocking allows the test heads to maintain good workpiece contact as the band flexes. In the disclosed embodiment each test head is connected to the band by a pair of rivets whose axes locate a plane which, when the apparatus is in use, is parallel to the workpiece travel path.

Each test head is equipped with a pair of spaced parallel wear shoes. These wear shoes are, when the device is in use, disposed transversely of the path of travel. If the workpiece is cylindrical, as an example, the wear shoes are in line contact with the workpiece in the plane located by the rivet axes. This line contact of the wear shoes of a test head establishes a "rocking" axis for that test head.

Each test head has a recess between its spaced wear shoes. The band is disposed in those recesses and secured to each test head by its rivet pair and thus held in close, but spaced, relationship with the workpiece by the test heads when the apparatus is in use.

Several advantages over prior devices are realized by using the test apparatus made in accordance with this invention. One advantage is the test probes remain in testing contiguity with a workpiece surface notwithstanding cross-sectional variations in the workpiece. Another advantage is the apparatus accommodates testing of a wide variety of workpieces without the need for adjustments or interchanging the test probe sets.

A further advantage of an apparatus made in accordance with this invention is that a single testing system equipped with a plurality of the test apparatuses of this invention mounted in a manner similar to that taught by Baker et al can be used for inspection of the total surface of products of a variety of cross-sectional configurations without changing the overall system. For example a single test system can be used for the inspection of either a billet or a pipe.

Accordingly an object of this invention is to provide a novel and improved flaw detection mechanism and a method of flaw detection with which a variety of objects may be inspected without change or adjustment of the test mechanism.

Other objects and advantages and a fuller understanding of the invention will be appreciated from the following detailed description and the accompanying drawings.

BRIEF DESCRIPTION OF DRAWINGS

FIG. 2 is a sectional view of a test probe on an enlarged scale, as seen from the plane indicated by the line 2—2 of FIG. 1;

FIG. 3 is a sectional view of the pipe and the test apparatus as seen from the plane indicated by the line 3—3 of FIG. 1 and is also a phantom view of the test apparatus showing it spaced from the workpiece;

FIG. 4 is a sectional view similar to FIG. 3 but showing the testing of a billet; and, FIG. 5 is an enlarged perspective view, partially in fragmentary form, showing the spring biased connection of the test apparatus made in accordance with the present invention.

BEST MODE FOR CARRYING OUT THE INVENTION

Figure 1:
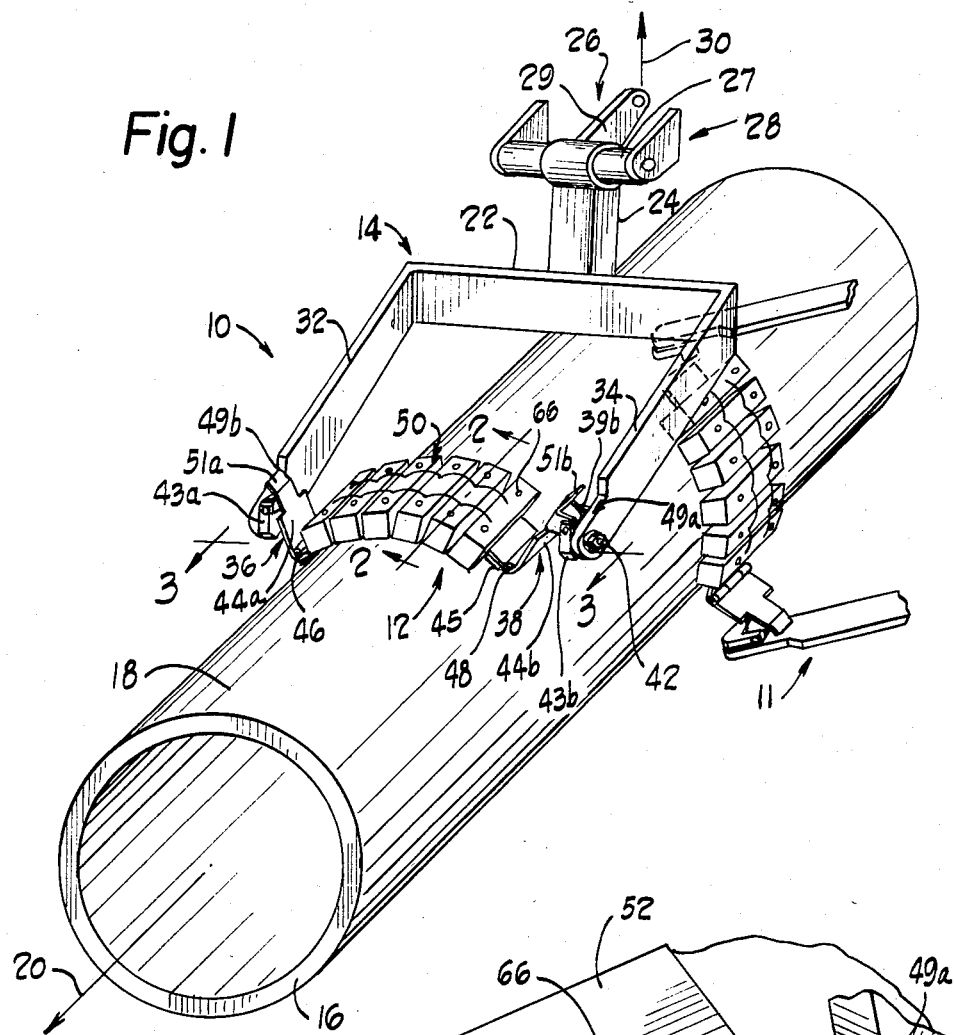
FIG. 1 is a perspective view partially in fragmentary form showing two of a circumscribing set of test apparatuses made in accordance with the present invention and positioned to inspect a pipe.

Referring to FIG. 1, two of a set of test apparatuses are shown at 10, 11. In use, where total inspection of a surface of a workpiece is to be accomplished, a set of a sufficient number of these apparatuses is provided to surround the workpiece. For clarity of illustration only the apparatuses 10, 11 are shown in FIG. 1 and only 10 will be described in detail since the others are identical to it. For a more complete description of a mechanism suitable for mounting a set of detector apparatuses in workpiece surrounding relationship, reference is made to U.S. Pat. No. 4,101,832 to Baker et al and that patent is herein incorporated by reference in its entirety.

Each test apparatus 10 includes a flexible probe assembly 12. A clevis in the form of a squared U-shaped configuration is shown at 14. The clevis serves to position the flexible probe assembly in testing relationship with a workpiece which in FIG. 1 is in the form of a pipe 16. The pipe 16 has a cylindrically contoured surface 18 which is to be inspected for surface flaws. To effect the inspection in the preferred arrangement, the workpiece is moved axially along a path of travel indicated by the arrow 20.

Each clevis 14 includes a central section 22. The central section 22 is connected to a support arm 24 of a lever 26. The lever 26 is journalled for rotation on a shaft portion 27 of a lever support assembly 28. The lever 26 includes a power arm 29 which is connected to a test apparatus lever actuator, not shown, but indicated by an arrow 30.

When force is applied by the lever actuator 30 to the power arm 29 in a direction radially toward the workpiece travel path, the associated test apparatus 10 is shifted to a parked position shown in phantom in FIG. 3. When forces are applied to the lever arm in the opposite direction, the clevis is moved to an inspection position and the test apparatus is moved into testing contiguity and contact with a workpiece as shown in FIGS. 1, 3 and 4.

The clevis 14 includes a spaced pair of arm sections 32, 34 fixed to the central section 22. The arm sections extend along paths longitudinal of the path of travel and carry, near the ends remote from the central section, the flexible probe assembly 12. A pair of hinges 36, 38 are provided and respectively connected to the clevis arm sections 32, 34 by axially aligned pivots 40, 42. The hinges 36, 38 respectively include mounting portions 43a, 43b which are respectively pivotally secured to the associated arm sections 32, 34 by the pivots 40, 42. Washers 47a, 47b are shown that respectively space the mounting portions 43a, 43b from their associated arm section 32, 34. The hinges 36, 38 respectively include connecting portions 44a, 44b. The hinge portions 43a, 44a and 43b, 44b are respectively hinged together by pintles whose axes, when the device is in use, are parallel the path of relative travel between a workpiece and the flexible probe assembly. The hinges respectively include torsion springs 39a, 39b.

Figure 5:
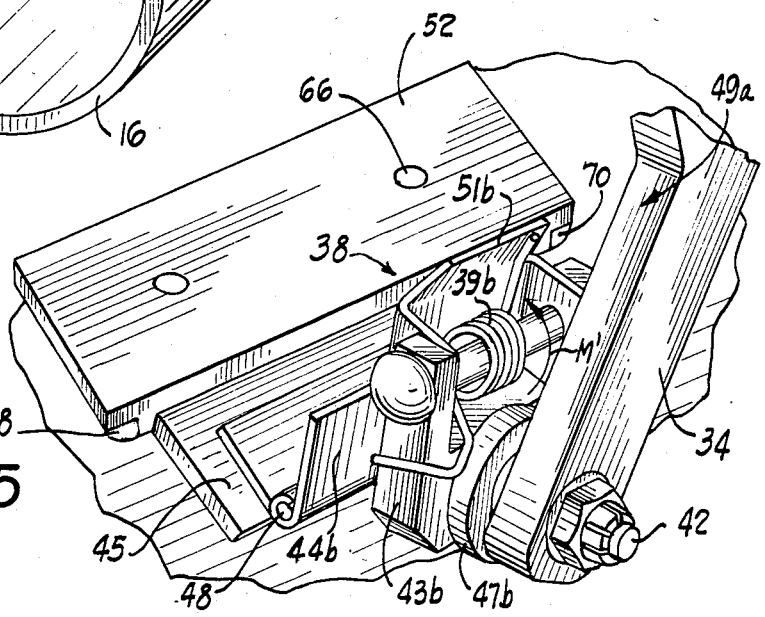

As is best seen in FIG. 5, the spring 39b has a coiled section around the pintle of hinge 38 and end portions which respectively act against the mounting and connecting portions of the hinge. The spring 39a is the mirror image of the spring 39b. Thus the spring end portions are operatively coupled to their associated connecting and mounting portions to bias the connecting portions 44a 44b toward a test head storage position shown in phantom in FIG. 3 and in the directions shown by the arrows m, m'. The connecting portions are against the mounting portions when the test apparatus is not in use.

The probe assembly 12 includes a flexible band member 45. The flexible band member 45 is pivotally connected at 46 and 48 to the connecting portions 44a, 44b respectively. The spring biased hinges 36, 38 tension the flexible band 45 between the arm sections 32, 34. The flexible band member is made from suitable non-magnetic material such as plastic or stainless steel.

Each of the clevis arm sections 32, 34 respectively has a cut out portion 49a, 49b to permit clearance of top parts 51a, 51b respectively of the connecting portions when the connecting portions are pivoted away from the mounting portions.

A plurality of test heads 50 are shown. Referring to FIG. 2 where a test head is shown on an enlarged scale, the test head includes a body 52 which is preferably formed of suitable plastic. A detection coil or probe 54 is embedded in the body 52. The probe 54 includes a central portion 56 of windings which are wound in one direction and spaced end portions 58 which together have a like number of oppositely wound windings. The opposite windings are to provide self quenching of spurious signals in a known manner. Each probe 54 is connected to suitable flaw detection circuitry, not shown, by leads 60.

Each probe body 52 includes a recess 62 having a top body surface 64. The flexible band member 45 abuts the surface 64 and is held in engagement with it by a spaced pair of fasteners in the form of rivets 66. The rivets 66 have axes which locate a plane that, when the mechanism is used to inspect a cylindrically contoured object such as the pipe 16, is parallel to the axis of the travel path as indicated by the arrow 20, FIG. 1.

Each test head includes a spaced pair of wear shoes 68, 70 which are transverse to the travel path and are designed to provide test probe engagement with a workpiece being inspected. When the workpiece is cylindrical, each pair of wear shoes 68, 70 is in line contact with the workpiece and the lines of contact are circumferentially spaced and aligned. Each such line of contact is substantially in the plane located by the rivet axes of its probe. Each line contact delineates a rocking axis for its probe to rock back and forth as it is maintained in surface contact with the workpiece being inspected.

In operation, referring to FIG. 3, the pipe 16 is positioned for transportation along the work path. Each test apparatus 10 is then moved from a storage position indicated in phantom lines in FIG. 3 to the test position shown in solid lines in FIGS. 1 and 3. As the test apparatus is moved through actuation of the lever 24, the wear shoes 68, 70 of each of the test heads 50 are sequentially brought into workpiece engagement. This progressive engagement starts with the central test head and progresses outwardly as the clevis 14 is moved toward the workpiece.

This motion continues toward the workpiece until (a) all of the test head wear shoes are in engagement with the workpiece, (b) the flexible band 45 has been flexed by tension into generally concentric relationship with the workpiece, and (c) the hinges have moved to the positions indicated in FIG. 3 in solid lines to accommodate this band flexing. Pressure is maintained on the probe assembly 12 during a flaw inspection procedure through the combined action of the lever actuator indicated by the arrow 30, the flexible band, the clevis and action of the hinges. Alignment of the test heads longitudinally of the path of workpiece travel is accommodated by rotation of the hinges about the axially aligned pivots 40, 42.

As FIG. 4 shows, a major advantage of the test apparatus of this invention is that the apparatus shown as inspecting a pipe in FIGS. 1 and 3 is quite well suited for inspection of a billet 72. This billet inspection is accomplished without need for any adjustment or substitution of different detector sets. A comparison of FIGS. 3 and 4 will also show that the flexible band 45 has in each case taken a configuration generally complemental to that portion of the workpiece being inspected even though the configurations of the two workpieces are considerably different. In FIG. 3, the planes defined by the rivet axes are all disposed generally radially of the workpiece and the travel path axis. In FIG. 4 the outermost probes are positioned such that their rivet axes planes are generally perpendicular to the flat sides of a generally square billet while the centermost test heads have rocked to accommodate inspection of the rounded corner of the billet. Expressed another way, the test apparatus of this invention is constructed such that the flexible probe assembly will contour itself to adapt to the inspection of any convexly shaped or flat workpiece surface.

Although the invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

I claim:

1. A test apparatus for use in non-destructive testing of a workpiece having a contoured external surface, said apparatus comprising:
   a flexible probe assembly including a plurality of spaced test heads and securing means to flexibly secure said plurality of test heads to each other such that a test head is adjacent at least one other test head, the plurality of adjacent test heads when in use being spaced transversely to a workpath of such workpiece;
   urging means operatively connected to said flexible probe assembly for urging said flexible probe assembly into contact with such external surface of such workpiece; and,
   tensioning means for tensioning said flexible probe assembly as the urging means brings the probe assembly into contact with the workpiece so that the urging and tensioning means co-act to bring said probe assembly into conformity with at least a portion of such external surface to maintain said plurality of test probes in juxtaposition with such surfaces of a workpiece as such workpiece and the assembly move relatively along said workpath.

2. A test apparatus for use with a contoured surfaced workpiece having a generally convex outer surface the apparatus being for non-destructive testing of a workpiece when a workpiece and the apparatus are relatively moved along a travel path, said apparatus comprising:
   a flexible probe assembly including a flexible band member having ends spaced transversely with respect to said travel path and a plurality of spaced test heads fixed to and spaced along said band member between said ends;
   urging means operatively connected to said flexible band member for urging said flexible probe assembly against a workpiece; and
   tensioning means coupled to said flexible band member to exert a tensioning force on said flexible band to bring said band when in use into conformity with at least a portion of such convex outer surface between said ends to maintain said plurality of test probes in juxtaposition with such surface.

3. A test apparatus according to claim 2 wherein each of said test heads includes a probe support body fixed to said flexible band member and a test probe located within said probe support body.

4. A test apparatus according to claim 2 wherein each of said test head assemblies further includes spaced wear shoes each projecting from the remainder of its assembly to contact such workpiece when in use whereby to prevent wearing of the other portions of the flexible probe assemblies.

5. A test apparatus according to claim 2 wherein said urging means is a clevis connected to said flexible band member, said clevis applying urging forces to said flexible band member.

6. A test apparatus for use with a contoured surfaced workpiece having a generally convex outer surface, the apparatus being for non-destructive testing of a workpiece when a workpiece and the apparatus are relatively moved along a travel path, said apparatus comprising:
   a continuous flexible band having, when in use, ends spaced transversely with respect to said travel path;
   a plurality of spaced test heads fixed to said band, each test head including a probe body and a test probe located within said probe body; and a clevis assembly connected to said flexible band member, said clevis assembly being adapted to apply urging forces to said flexible band member to urge said flexible band member and said test heads toward a workpiece, said test heads being adapted to contact at least a portion of such workpiece, said flexible band member, when in use, being spaced from the workpiece by said test heads; and means coupled to said flexible band member ends adapted to tension said band as said clevis assembly forces said test heads into contact iwth at least a portion of such convex workpiece surface to cause at least some of said spaced test heads to conform to said convex surface.

7. A test apparatus according to claim 6 wherein said clevis assembly includes a clevis connected to said flexible band member by two spaced double hinged, spring biased connecting members, each being pivotably connected to said flexible band member and to said clevis and applying tension to said ends of said flexible band member by said spring bias.

8. A test apparatus according to claim 6 wherein each test head is fixed to said flexible band for rocking motion transverse such travel path.

9. A test apparatus according to claim 6 wherein each of said test heads further includes spaced wear shoes each projecting from the remainder of its assembly for contacting such workpiece during inspection.

10. A test apparatus for use in non-destructive testing of a convex outer surface of a contoured surfaced workpiece when the workpiece and the apparatus are relatively moved along a travel path, said apparatus comprising:

a generally U-shaped clevis including spaced, longitudinally extending arms;

a flexible band extending tranversely of and between said arms, said flexible band being movably connected to said clevis;

a plurality of spaced, elongated test heads secured to said flexible band, each of said test heads having a test probe located therein;

means for positioning said clevis in proximity to a workpiece to urge the test heads into contact with at least a portion of such convex workpiece surface; and tensioning means for tensioning said flexible band member for co-acting with the means for positioning as said test heads are urged when in use into contact with such surface to provide conformity between such workpiece portion and said flexible band such that each test head is juxtaposed to such workpiece.

11. The test apparatus of claim 10 wherein, when in use, said flexible band is maintained spaced from a workpiece by said test heads.

12. The test apparatus of claim 10 wherein each of said test heads is fixed to said flexible band in a manner which permits movement about an axis transverse to the band.

13. The test apparatus of claim 10 wherein the test heads each include spaced wear elements each projecting from the remainder of its assembly to contact a workpiece during inspection.

14. A test apparatus for use in non-destructive testing an external region of a contoured surfaced workpiece when the workpiece and the apparatus are relatively moved along a travel path, said apparatus comprising:

a flexible probe assembly including an elongated flexible member disposed when in use transversely with respect to said travel path, the assembly also including a plurality of spaced test heads fixed at spaced locations to said elongated member;

an urging means connected to said flexible assembly for urging said flexible assembly against a workpiece, and tensioning means for tensioning said flexible member to co-act with said urging means to bring the assembly into conformity with at least a portion of an outer surface to maintain said plurality of test heads in testing contiguity with said outer surface of such workpiece.

15. A test apparatus for use in non-destructive testing of a contoured surfaced workpiece when the workpiece and the apparatus are relatively moved along a travel path, said apparatus comprising:

a continuous flexible band member disposed when in use transversely with respect to said travel path;

a plurality of spaced test heads fixed to said band member, each test head having a probe body and a test probe located within said probe body; and, a clevis assembly connected to said flexible band member through a spring biased double hinge connection, said clevis assembly being adapted to apply urging forces to said flexible band member to urge said flexible band member and said test heads toward said object to bring the test heads when in use into juxtaposed relationship with at least a portion of such workpiece surface, said flexible band member being spaced from such surface by said test heads and tensioned by the spring biased connection to maintain the plurality of test heads in scanning relation to the workpiece.

16. A method for providing non-destructive testing contiguity between a number of connected test heads and at least a portion of a convex outer surface of a workpiece comprising the steps of:

(a) tensioning a flexible band member having a plurality of affixed test heads;

(b) moving said flexible band member toward said workpiece surface until said test heads contact the outer surface of said workpiece;

(c) continuing the movement until said flexible band is tensioned in conformity with said at least a portion of said outer surface of said workpiece; and, (d) relatively moving the workpiece and test heads longitudinally of the workpiece while concurrently determining the location of flaws at the workpiece surface.

17. A process for locating flaws in an elongated workpiece having an external surface of generally uniform, non-concave, cross-sectional configuration with an inspection apparatus of the eddy current type, comprising:

(a) bringing at least one wear shoe of each of a plurality of equally spaced test heads connected by a flexible coupling into engagement with such external workpiece surface to allow the equally spaced test heads to move relatively to each other into engagement with the workpiece until all test heads have at least one wear shoe in longitudinally extending line of workpiece contact;

(b) relatively moving the workpiece and test heads longitudinally of the workpiece while concurrently applying a force to the test heads urging their wear shoes into workpiece engagement and allowing each of the test heads to rock about its longitudinally extending line of workpiece contact; and, (c) determining the location of flaws in the workpiece concurrently with the performance of such relative moving.

18. A method for providing non-destructive testing contiguity with at least a portion of a surface of a workpiece comprising the steps of:

(a) tensioning a flexibly interconnected set of relatively moveable test heads with wear shoes;

(b) moving said set of test heads toward said workpiece;

(c) contacting at least one test head against the workpiece;

(d) continuing the movement to cause sequential contact of other heads of the set and further continuing the movement until said set is tensioned in conformity with said at least a portion of said surface of said workpiece and the other test heads of the set contact said workpiece;

(e) relatively moving the workpiece and test heads longitudinally of the workpiece while concurrently applying a force to the test heads urging their wear shoes into workpiece engagement; and, (f) determining the location of flaws in the workpiece concurrently with the performance of such relative moving.

* * * * *